United States Patent
Boit et al.

(10) Patent No.: US 9,346,726 B2
(45) Date of Patent: May 24, 2016

(54) PROCESS FOR PRODUCING COMPOSITIONS RICH IN CRYSTALS OF MANNITOL IN DELTA FORM, COMPOSITIONS AND CRYSTALS OBTAINED AND USES THEREOF

(71) Applicant: ROQUETTE FRERES, Lestrem (FR)

(72) Inventors: Baptiste Boit, Bethune (FR); Laurent Rossi, Arras (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/420,724

(22) PCT Filed: Aug. 7, 2013

(86) PCT No.: PCT/FR2013/051907
§ 371 (c)(1),
(2) Date: Feb. 10, 2015

(87) PCT Pub. No.: WO2014/027158
PCT Pub. Date: Feb. 20, 2014

(65) Prior Publication Data
US 2015/0218071 A1    Aug. 6, 2015

(30) Foreign Application Priority Data
Aug. 17, 2012 (FR) ..................... 12 57859

(51) Int. Cl.
*C07C 29/80* (2006.01)
*C07C 29/86* (2006.01)
*C07C 29/78* (2006.01)
*C07C 31/26* (2006.01)

(52) U.S. Cl.
CPC .............. *C07C 29/78* (2013.01); *C07C 31/26* (2013.01); *C07B 2200/13* (2013.01); *C07C 29/80* (2013.01); *C07C 29/86* (2013.01)

(58) Field of Classification Search
CPC .............................. C07C 29/80; C07C 29/86

USPC ............................................. 568/868
See application file for complete search history.

(56) References Cited

U.S. PATENT DOCUMENTS

2013/0261346 A1    10/2013    Erdmann et al.

FOREIGN PATENT DOCUMENTS

| WO | 2008/147811 A1 | 12/2008 |
| WO | 2012/079671 A2 | 6/2012 |

OTHER PUBLICATIONS

Burger A et al.: "Energy/temperature diagram and compression behavior of the polymorphs of D-mannitol", Journal of Pharmaceutical Sciences, American Pharmaceutical Association, Washington, US, vol. 89, No. 4, Jan. 1, 2000, pp. 457-468, XP003002443, ISSN: 0022-3549, DOI: 10.1002/(SICI)1520-6017(200004)89:4<457::ID-JPS3>3.0.CO;2-G cited in the application figure 5-, tables 1-2.
Botez et al.: "Crystal Structure of anhydrous δ D-mannitol", Department of Physics and Astronomy, State University of New York, Stony Brook, New York 11794-3800, Powder Diffraction 18 (3), Sep. 2003, (Received Jan. 23, 2003; accepted Apr. 22, 2003), pp. 214-217.
International Search Report, dated Oct. 15, 2013, from corresponding PCT application.

*Primary Examiner* — Elvis O Price
(74) *Attorney, Agent, or Firm* — Young & Thompson

(57) ABSTRACT

A process for producing a composition which is particularly rich in D-mannitol, the latter being present in the form of crystals having a volume average diameter greater than 20 pm, wherein the crystals correspond to a very large extent to the δ polymorph. This process makes use of the evaporative crystallization technique, in which the seeding and then the controlled growth of the crystals is carried out at different evaporation rates. Finally, very pure δ crystals are advantageously obtained, which have a better compressibility than the α and β homologues thereof and which, by virtue of the sizes thereof, result in a powder which is not subject to caking.

9 Claims, 2 Drawing Sheets

PARTECK™ M

CRYSTALS ACCORDING TO THE INVENTION

PROCESS FOR PRODUCING COMPOSITIONS RICH IN CRYSTALS OF MANNITOL IN DELTA FORM, COMPOSITIONS AND CRYSTALS OBTAINED AND USES THEREOF

The subject of the present invention is a process for producing a composition which is particularly rich in D-mannitol, the latter being present in the form of crystals having a volume mean diameter D4,3 greater than 20 μm, said crystals corresponding to a very large extent to the δ polymorph. This process makes use of the evaporative crystallization technique, in which the seeding and then the controlled growth of the crystals is carried out at different evaporation rates. Finally, δ crystals are advantageously obtained, which have a better compressibility than the α and β homologs thereof and which, by virtue of the sizes and the purity thereof, result in a powder which is not subject to caking.

Mannitol is an acyclic polyol commonly used in particular as an excipient in pharmaceutical formulations such as tablets, granules or powders, or else as a stabilizer in protein compositions. There are three real polymorphs of D-mannitol: the α, β and δ polymorphs. In the present application, the term "polymorph" is intended to mean a solid crystalline structure of D-mannitol which is identifiable, as subsequently explained in detail, by a particular X-ray diffraction spectrum. The term α, β or δ "form" may also be used in the present application instead of the term "polymorph".

Methods of structural determination which are based on X-ray diffraction data are particularly used for studying D-mannitol polymorphs, for two main reasons (C. E. Botez et al. Powder diffraction 2003, 18(3), 214). First of all, determination of the crystalline structure via X-rays enables a precise, direct and unequivocal identification of a given polymorph. Modern diffraction data analysis techniques then make it possible to study complex diffraction profiles and it is thus possible to identify the exact content of a powder composed of a mixture of several polymorphs.

Consequently, this technique is perfectly mastered by those skilled in the art and allows them in particular to quantify, within a crystalline composition, the proportion of each polymorph. This quantification means, for example, a percentage by weight of a given polymorph relative to the total weight of the crystalline composition. It is precisely this type of quantification which is used in the present application.

It is known that the crystallization of D-mannitol results in the formation of a given polymorph or of a given mixture of polymorphs depending on the conditions of the crystallization process, such as the solvent, the concentration, the temperature, etc. (C. E. Botez et al. Powder diffraction 2003, 18(3), 214).

Each of the α, β and δ structures has specific physical characteristics, in particular in terms of solubility, hygroscopicity and compressibility. By way of example, the β form is a crystalline form which is thermodynamic and stable under standard ambient conditions, the α and δ crystalline forms being forms that are metastable under these same conditions.

An essential characteristic for an excipient is the compressibility thereof: it reflects the ability of said excipient to form tablets by direct compression. The α, β and δ polymorphs of mannitol do not all have the same compressibility (A. Bruger et al., J. Pharm. Sci. 2000, 89, 457), the δ polymorph having the highest compressibility compared with the α and β homologs thereof. It is therefore advantageous to have industrial methods which readily and less expensively result in the production of D-mannitol powders rich in δ polymorph.

D-Mannitol is obtained from the catalytic hydrogenation of a fructose syrup, which results in the obtaining of a mixture of sorbitol and mannitol. A conventional crystallization process then makes it possible to recover the D-mannitol crystals, but it is noted that, industrially, it results in the predominant formation of the β polymorph.

Alternatively, small amounts of D-mannitol in δ polymorph form can be produced by cooling an aqueous solution of D-mannitol to 0° C. and then by rapidly isolating the resulting δ forms, before they are converted into α and β polymorphs (A. Bruger et al., J. Pharm. Sci. 2000, 89, 457). However, this is again a process of which the yield is insufficient to be transposable to an industrial scale.

Document WO 2012/079671 discloses a process which consists in placing a D-mannitol solution in suspension in a gas and in drying the material in order to obtain crystalline particles of D-mannitol. The D-mannitol thus obtained comprises more than 98% by weight of δ polymorph, and has a median diameter X50 of 200, 300 or 450 μm (cf. examples 1, 2 and 3).

Document WO 2008/147811 provides, for its part, a process which consists in producing an initial solution of D-mannitol in an appropriate solvent such as water, in adding an auxiliary agent such as D-sorbitol, and in carrying out the solidification of D-mannitol in δ form. This solidification can alternatively be carried out by evaporation, by adding an antisolvent, by thermal microscopy or, preferentially, by cooling. It is indicated that the cooling of the solution should not be rapid, the temperature reduction rate disclosed in the examples being 1° C. per minute.

Seeking to reproduce the tests of the abovementioned document, at cooling rates of 1° C. per minute but also at lower rates according to the teaching of said document, the applicant has made the following double finding: not only were the crystals obtained not systematically in δ form, but they had a relatively low volume mean diameter, namely between 10 μm and 20 μm.

With regard to the latter characteristic, a certain number of points regarding the problems created by the presence of crystals of small sizes should be specified. First of all, crystals of excessively small sizes are difficult to separate from the mother liquors. The washing operation to remove the surface impurities is subsequently made more complex by virtue of the small size of the crystals to be treated. Finally, it is well known that, in the case of a powder, the smaller the size of the crystals, the more the pulverulent powder or composition comprising said crystals will be subject to caking. Consequently, the process as disclosed in the abovementioned document cannot give satisfaction.

Finally, the applicant is also aware of a commercial composition of D-mannitol crystals in δ form. Said composition is sold by the company Merck™ under the name Parteck™ Delta M. By analyzing this powder, the applicant has shown that it is not a question solely of δ polymorphs: the content by dry weight of δ polymorphs represents approximately 90% of the total crystals (concomitant presence of crystals in β form). Starting from this observation, the applicant has then demonstrated that the stability of this product with respect to humidity is not satisfactory: this constitutes a totally unacceptable element for a product intended to be used as an excipient, and therefore liable to be stored over long periods of time in atmospheres which are humid to a greater or lesser extent.

Consequently, there is an as yet unsatisfied need to have a process for producing D-mannitol crystals in δ form, having a sufficiently high yield to make it industrializable, resulting in crystals of high purity and the volume mean diameter of which is at least equal to 20 μm in order to facilitate the crystal rinsing steps and to avoid caking of the powder, while at the same time resulting in a final product having good stability with respect to humidity.

While continuing research along these lines, the applicant has succeeded in developing such a process. Said process is based on the use of the evaporative crystallization technique, in which both the crystal nucleation step and the crystalline growth step are controlled by adjusting the evaporation rates according to the mass of the solution to be evaporated. The applicant has in particular succeeded in identifying the parameters which make it possible to control these 2 steps, so as to result in the end in a solid or powder which is more than 97% by dry weight made up of D-mannitol, the D-mannitol crystals being more than 98% by dry weight represented by the δ polymorph, said crystals of δ form having a volume mean diameter greater than 20 μm.

A first subject of the present invention therefore consists of a process for producing a composition comprising D-mannitol crystals of δ form, of which more than 97%, preferentially more than 98% and very preferentially more than 99% by weight of the dry matter thereof consists of D-mannitol, said process comprising the steps of:
producing an initial stock solution of D-mannitol in a solvent, in the presence of an auxiliary agent,
evaporating said solvent so as to carry out the crystallization of the D-mannitol, through a seeding phase and a crystal growth phase,
characterized in that:
during the seeding phase: an evaporation rate by mass of between 0.08 and 0.5 kg of solvent/h/kg of initial stock solution, more preferentially between 0.1 and 0.2 kg of solvent/h/kg of initial stock solution, is applied;
during the growth phase: an evaporation rate by mass of between 0.005 and 0.1 kg of solvent/h/kg of initial stock solution, more preferentially between 0.01 and 0.05 kg of solvent/h/kg of initial stock solution, is applied.

For the purposes of the invention, the term "composition" is directed toward both a pulverulent composition and a powder of D-mannitol crystals or crystalline powder.

The first step of said process therefore consists in producing an initial stock solution of D-mannitol in a solvent in the presence of an auxiliary agent, by introducing the various constituents into the solvent. This step is preferentially carried out with stirring, and at a temperature which allows complete dissolution of the D-mannitol and of the auxiliary agent, for example between 70 and 100° C.

The solvent is any solvent or mixture of solvents in which D-mannitol is soluble, and in which the auxiliary agent is also soluble. It may be acetone or water, and preferentially water.

The D-mannitol used is advantageously that which is produced from the catalytic hydrogenation of fructose, as already discussed. Typically, the D-mannitol used is in β form and has a D-mannitol richness of between 10% and 99% by dry weight, for example the D-mannitol Pearlitol™ 50C sold by the applicant company.

The auxiliary agent is a crystallization auxiliary agent which assists the crystallization of D-mannitol. The auxiliary agent can be chosen from sorbitol, citric and glycolic acids, fructose, mannose, mineral salts such as sodium chloride, potassium chloride or calcium chloride and mixtures thereof; it is preferably sorbitol, for example the sorbitol Neosorb™ P60 sold by the applicant company. The D-mannitol:auxiliary agent ratio may be from 20:80 to 80:20 by weight.

The initial stock solution produced has a dry matter content of between 20% and 70% and preferably of between 30% and 60%. It has a D-mannitol richness of between 30% and 80% and preferably of between 40% and 60% by weight of dry matter. It is clearly understood that reference is being made here to the initial stock solution, as prepared before the solvent evaporation step.

The second step of the process according to the invention consists in evaporating the solvent, by providing heat by means of a heat exchanger. This step is carried out with stirring and under vacuum. An absolute vacuum of between 30 mbar and 300 mbar, preferably of between 50 and 150 mbar, is preferentially applied. It is during this step that the crystallization of the D-mannitol takes place in 2 steps or 2 phases: the crystals first of all appear (this is the seeding phase) and then these crystals develop (this is the crystalline growth phase).

The distinction between these 2 phases is made visually: the appearance of crystals visible to the naked eye (whitening of the solution) corresponds to the transition between the seeding step and the growth step. This moment marks the change in the operating conditions as defined above, i.e. the decrease in the evaporation rate by mass. Preferentially, it is chosen to wait for a period of time of between 5 and 15 minutes starting from the appearance of the first crystals before modifying the evaporation rate. For those skilled in the art used to carrying out crystallization experiments, the distinction between these 2 phases is routine practice. What is more, experiments carried out by the applicant on 2 different scales have demonstrated the very great ease with which these 2 phases can be identified, both at the level of a laboratory test and at the level of a "pilot" experiment.

More specifically, during the seeding phase, an evaporation rate by mass of between 0.08 and 0.5 kg of solvent/h/kg of initial stock solution, more preferentially between 0.1 and 0.2 kg of solvent/h/kg of initial stock solution, is applied.

Practically, those skilled in the art impose an evaporation rate by adjusting the temperature of the heat exchanger: typically, by adjusting the temperature of a coil connected to a thermostated oil bath. On the basis of simple routine tests, they succeed in determining the temperature on an ad hoc basis resulting in a given evaporation rate by mass.

More specifically, during the growth phase, an evaporation rate by mass between 0.005 and 0.1 kg of solvent/h/kg of initial stock solution, more preferentially between 0.01 and 0.05 kg of solvent/h/kg of initial stock solution, is applied. One of the keys of the present invention is therefore based on the choice of this double evaporation rate ramp: rapid during the seeding phase, slower during the crystalline growth phase.

Figure 1:
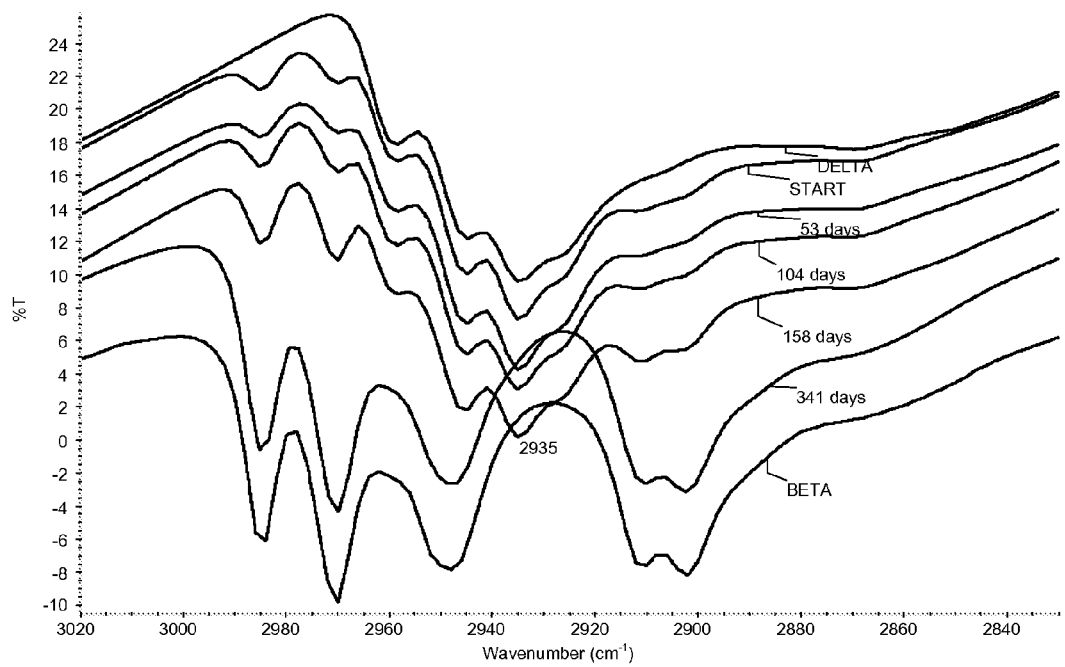
FIGS. 1/2 and 2/2 are Qualitative IR spectra of the commercial product and the product according to the invention.
Figure 2:
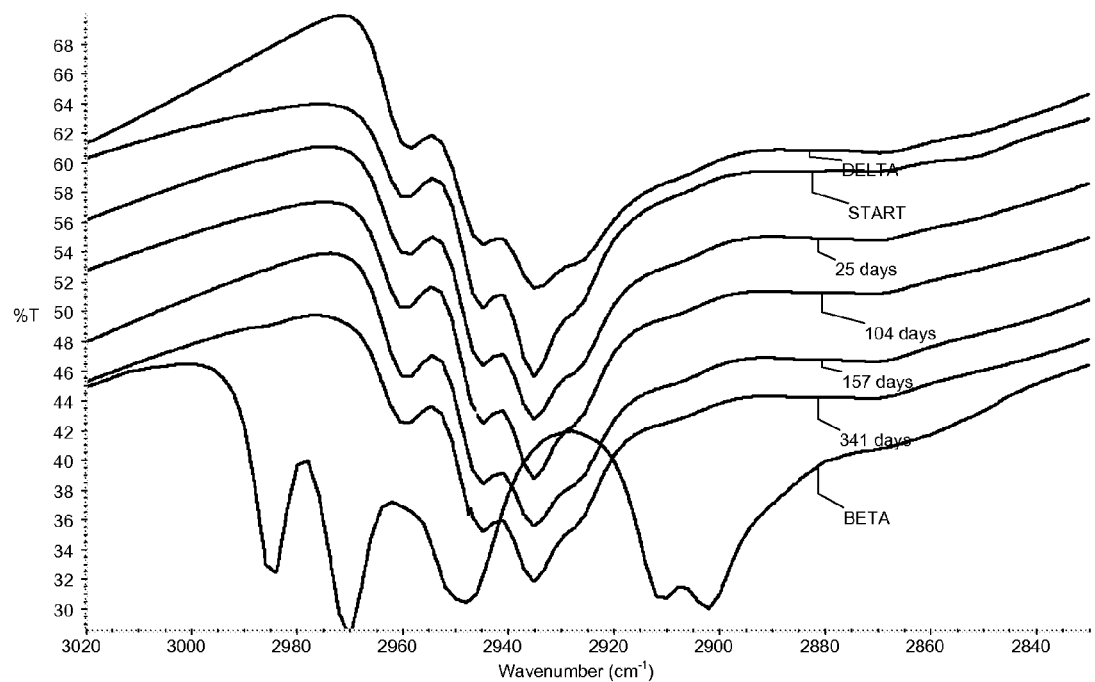

More particularly, a subject of the invention is a process for producing a composition, comprising D-mannitol crystals of delta (δ) form, of which more than 97%, preferentially more than 98% and very preferentially more than 99% by weight of the dry matter thereof consists of D-mannitol, said process comprising the following steps:
producing an initial stock solution of D-mannitol in a solvent, in the presence of an auxiliary agent,
evaporating said solvent so as to carry out the crystallization of the D-mannitol, through a seeding phase and a crystal growth phase,
characterized in that
during the seeding phase: an evaporation rate by mass of between 0.08 and 0.5 kg of solvent/h/kg of initial stock solution, more preferentially between 0.1 and 0.2 kg of solvent/h/kg of initial stock solution, is applied;

during the growth phase: an evaporation rate by mass of between 0.005 and 0.1 kg of solvent/h/kg of initial stock solution, more preferentially between 0.01 and 0.05 kg of solvent/h/kg of initial stock solution, is applied, and in that the evaporation step is carried out with stirring and under an absolute vacuum of between 50 mbar and 100 mbar;

the solvent is water;

the auxiliary agent is sorbitol.

In addition, the process according to the invention comprises a step of separating the crystals from the solution, in particular by centrifugation or suction filtration. This step is then followed by a clarifying (rinsing) step which consists in surface-cleaning the crystals produced, by rinsing them in a solvent. Preferentially, this step consists in carrying out a first rinsing with cold water (water of which the temperature is between 5° C. and 25° C.), and then a second rinsing in a mixture of water and ethanol.

Finally, the process according to the invention comprises a drying step, aimed at evaporating the solvent from the composition produced.

The process which is the subject of the invention has in particular the advantage of enabling the production, with a high yield and a high degree of purity, of a composition of D-mannitol predominantly in the form of crystals of delta (δ) form, in particular of a pulverulent composition or powder of D-mannitol predominantly in the form of crystals of delta (δ) form (more than 98% by dry weight of D-mannitol crystals), said crystals having a volume mean diameter D4,3 greater than 20 μm, preferentially a volume mean diameter of between 30 μm and 100 μm and very preferentially between 50 μm and 100 μm.

Another subject of the present invention consists of a composition comprising D-mannitol crystals, of which more than 97%, preferentially more than 98% and very preferentially more than 99% by weight of the dry matter thereof consists of D-mannitol, and characterized in that the D-mannitol crystals contain more than 98%, preferentially more than 99% and very preferentially more than 99.5% by dry weight of δ polymorphs. As already indicated, these % of δ polymorphs are determined by X-ray diffraction, a completely known and mastered technique which enables the quantification of the various crystalline populations in a powder.

This composition is also characterized in that said crystals have a volume mean diameter D4,3 greater than 20 μm, preferentially a volume mean diameter of between 30 μm and 100 μm and very preferentially between 50 μm and 100 μm. This volume mean diameter (arithmetic mean) D4,3 is determined on an LS 230 laser diffraction particle size analyzer from the company Beckman-Coulter™, equipped with its liquid measurement module, according to the technical manual and the specifications of the constructor. The crystals are dispersed in absolute ethanol with surfactant (in particular of "twin" type sold by Tego™).

This composition is in particular the composition that can be obtained using the process described above.

A subject of the present invention is thus also the composition, in particular the pulverulent composition or the powder, comprising D-mannitol crystals, which is capable of being obtained according to the process described above.

The composition which is the subject of the present invention has a dry matter content which consists of more than 97%, preferentially more than 98% and very preferentially more than 99% of D-mannitol and is in particular characterized in that the crystals contain more than 98%, preferentially more than 99% and very preferentially more than 99.5% by dry weight of δ polymorph, and in that said crystals have a volume mean diameter D4,3 greater than 20 μm, preferentially a volume mean diameter of between 30 μm and 100 μm and very preferentially between 50 μm and 100 μm.

This composition has in particular the advantage of being very compressible, not subject to caking and stable over time with respect to humidity.

The examples which follow make it possible to understand the present invention more clearly, without however limiting the scope thereof.

EXAMPLES

Example 1

This example illustrates the prior art, and more specifically the crystals as obtained under the conditions described and claimed in document WO 2008/147811. An aqueous stock solution of D-mannitol (Pearlitol™ 50C sold by the applicant company) and of D-sorbitol (Neosorb™ P60 also sold by the applicant) is first prepared. This mixture is prepared by introducing 20 mL of water and then D-mannitol and then D-sorbitol into a 150 mL jacketed thermostated beaker. The mixture is prepared with stirring (magnetic bar at a rotational speed of 50 revolutions/min), at a temperature of 80° C.

In tests No. 1, 4 and 6, a cooling rate of 1° C. per minute was applied, as described in document WO 2008/147811. Since said document also mentions that this rate should not be rapid, tests were also carried out at 0.1° C./min (tests No. 2, 5 and 7) and even at 0.05° C./min (test No. 8) and 0.01° C./min (test No. 3). The crystals obtained are recovered on a 0.45 μm Millipore filter. The crystalline form is analyzed by X-ray diffraction. The value of the volume mean diameter is also determined. These parameters along with the characteristics of the initial solution and the cooling rates appear in table 1.

In each of the 8 tests, a predominant polymorph was obtained (more than 99% by weight of the crystals consisting of this polymorph). It appears first of all that, under certain conditions (tests No. 3, 5 and 8), the β form is obtained rather than the δ form: the process according to document WO 2008/147811 does not therefore definitely result in the desired form. Furthermore, when the predominant form is indeed the δ form (test No. 1, 2, 4, 6, 7), the volume mean diameter of the crystals is systematically less than 20 μm.

TABLE 1

| Test No. | 1 | 2 | 3 | 4 | 5 | 6 | 7 | 8 |
|---|---|---|---|---|---|---|---|---|
| Mannitol/sorbitol ratio (dry/dry weight) | 42/58 | 42/58 | 42/58 | 62/38 | 62/38 | 50/50 | 50/50 | 50/50 |
| DM % | 39.5 | 39.5 | 39.5 | 39.7 | 39.7 | 50 | 50 | 50 |
| Rate ° C./min | 1 | 0.1 | 0.01 | 1 | 0.1 | 1 | 0.1 | 0.05 |
| Crystalline form (XR)* | delta | delta | beta | delta | beta | delta | delta | beta |

TABLE 1-continued

| Test No. | 1 | 2 | 3 | 4 | 5 | 6 | 7 | 8 |
|---|---|---|---|---|---|---|---|---|
| Volume mean diameter (μm) | 10 | 13 | Not measured | 14 | Not measured | 16 | 19 | Not measured |

*form present at more than 99% (by weight)

Example 2

The objective of this example is to illustrate, on the laboratory scale, the influence of the evaporation rates by mass during the seeding and growth steps, in a process for producing D-mannitol, under conditions according to the invention and outside the invention.

A stock solution at 50% of dry matter containing 50% by weight on a dry basis of Pearlitol™ 50C D-mannitol and 50% by weight on a dry basis of Neosorb™ P60 sorbitol is first of all prepared. The initial stock solution is heated to 80° C. so as to remove all traces of crystals.

Test No. 9

This test illustrates the invention. 5 kg of the initial stock solution are charged to a laboratory evaporative crystallizer having a volume equal to 5 L, equipped with a coil connected to a thermostated oil bath. Stirring is carried out by means of a Rushton turbine (150 revolutions/minute). The vacuum is regulated at 70 mbar. The temperature of the evaporative crystallizer exchanger is adjusted so as to obtain an evaporation rate by mass equal to 0.14 kg of water/h/kg of initial stock solution. This evaporation rate is maintained until 10 minutes after the appearance of the first crystals. The evaporation rate is then reduced to approximately 0.012 kg of water/h/kg of initial stock solution. The manipulation is stopped when 1 kg of water is evaporated. The crystals, or the powder or composition comprising the crystals, are then recovered, washed with cold water and then with an ethanol/water mixture (95%/5% by weight of each constituent) and oven-dried.

Tests No. 10 and 11

They illustrate domains outside the invention, and are carried out under the same conditions as the previous test. Only the evaporation rates vary.

TABLE 2

| Test No. | 9 | 10 | 11 |
|---|---|---|---|
| Invention/Outside Invention | IN | OI | OI |
| Seeding phase evaporation rate (kg of water/h/kg of initial stock solution) | 0.14 | 0.14 | 0.012 |
| Growth phase evaporation rate (kg of water/h/kg of initial stock solution) | 0.012 | 0.14 | 0.012 |
| End evaporated mass (kg) | 1 | 1 | 1 |
| Crystalline form XR* | delta | delta | beta |
| Mannitol content (% by dry weight) | 98.7 | 97.3 | Not measured |
| Volume mean diameter (μm) | 40 | 15 | Not measured |

*form present at more than 99% (by weight)

It is clearly demonstrated that, by applying the evaporation rates according to the invention during the seeding phase and during the growth phase, δ polymorphs and crystals having a volume mean diameter greater than 20 μm are obtained.

Example 3

The objective of this example is to illustrate, on the scale of an industrial pilot, the influence of the evaporation rates by mass during the seeding and growth steps, in a process for producing D-mannitol, under conditions according to the invention and outside the invention.

Tests No. 12 to 14

These tests illustrate the invention.

The same operations as previously are carried out, but on a pilot apparatus having a working volume of 500 L, and with 300 kg of stock solution. The vacuum is still 70 mbar. The stirring is carried out by means of a Rushton turbine (150 revolutions/minute). The condensates are recovered in a tank on a weigh scale. The separation and steps of washing with cold water and then with an ethanol/water mixture (95%/5% by weight of each constituent) are carried out on a Rousselet Robatel EHR 501 G turbine and the drying is carried out with a fluidized air bed.

Tests No. 15 and 16

They illustrate domains outside the invention, and are carried out under the same conditions as tests 12 to 14. Only the evaporation rates vary.

The results of table 3 demonstrate that it is indeed the double selection carried out with regard to the evaporation rates, both at the level of the seeding step and at the level of the growth step, which results in a composition comprising highly pure D-mannitol crystals which are extremely rich in δ polymorph and which have a volume mean diameter greater than 20 μm.

TABLE 3

| Test No. | 12 | 13 | 14 | 15 | 16 |
|---|---|---|---|---|---|
| Invention/Outside Invention | IN | IN | IN | OI | OI |
| Seeding phase evaporation rate (kg of water/h/kg of initial stock solution) | 0.133 | 0.133 | 0.133 | 0.133 | 0.133 |
| Growth phase evaporation rate (kg of water/h/kg of initial stock solution) | 0.033 | 0.05 | 0.015 | 0.001 | 0.15 |
| End evaporated mass (kg) | 85 | 85 | 85 | 85 | 85 |
| Crystalline form XR* | delta | delta | delta | beta | delta |
| Mannitol content (% by dry weight) | 99.5 | 99.0 | 99.5 | Not measured | 97.5 |
| Volume mean diameter (μm) | 80 | 60 | 97 | Not measured | 15 |

*form present at more than 99% (by weight)

Example 4

In this example, the stability with respect to humidity of a product according to the invention and the stability with respect to humidity of the product sold by the company Merck™ under the name Parteck™ Delta M are compared.

Firstly, an XR analysis of the crystals contained in the latter product demonstrates the presence of approximately 90% of δ polymorphs.

This product and the powder or composition resulting from test No. 12 according to the invention are then stored in a climatized chamber (20° C.) and at a controlled degree of relative humidity (75%). Qualitative IR spectra are produced on these 2 products at various moments, so as to monitor the evolution of the δ crystalline forms toward the β forms. These spectra are represented in FIGS. 1/2 and 2/2 respectively for the commercial product and for the product according to the invention.

It appears that the commercial product has completely changed to the β form after 341 days, which is not the case with the product according to the invention: the latter therefore has a greater stability with respect to humidity. This result is particularly advantageous with a view to an application in the pharmaceutical field: by having a δ form which is stable over time, it will be possible to produce granules with compressibility which is improved and prolonged over time, without affecting the bioavailability of the active ingredient contained in said granule.

The invention claimed is:

1. A process for producing a composition comprising D-mannitol crystals, of which more than 97% of the dry matter thereof consists of D-mannitol, said process comprising the steps of:
   producing an initial stock solution of D-mannitol in a solvent, and in the presence of an auxiliary agent,
   evaporating said solvent so as to carry out the crystallization of the D-mannitol, through a seeding phase and a crystal growth phase,
   wherein:
   during the seeding phase: an evaporation rate by mass of between 0.08 and 0.5 kg of solvent/h/kg of initial stock solution is applied;
   during the growth phase: an evaporation rate by mass of between 0.005 and 0.1 kg of solvent/h/kg of initial stock solution is applied;
   the evaporation rate during the seeding phase is different from the evaporation rate during the growth phase;
   the evaporation step is carried out with stirring and under an absolute vacuum of between 50 mbar and 100 mbar;
   the solvent is water; and
   the auxiliary agent is sorbitol.

2. The process as claimed in claim 1, wherein the production of the solution of D-mannitol in the solvent and in the presence of the auxiliary agent is carried out by mixing the constituents with stirring at a temperature which allows complete dissolution of the D-mannitol and of the auxiliary agent.

3. The process as claimed in claim 1, wherein the production of the initial stock solution of D-mannitol is carried out at a temperature of between 70° C. and 100° C.

4. The process as claimed in claim 1, wherein the initial stock solution has a dry matter content of between 20% and 70% by weight.

5. The process as claimed in claim 1, wherein the initial stock solution has a D-mannitol richness of between 30% and 80% by weight of dry matter.

6. The process as claimed in claim 1, wherein it comprises a clarifying step consisting in carrying out a first rinsing with cold water, and then a second rinsing in a solution of water and ethanol.

7. The process as claimed in claim 1, wherein it comprises a drying step.

8. The process as claimed in claim 1, wherein during the seeding phase the evaporation rate by mass is between 0.1 and 0.2 kg of solvent/h/kg of initial stock solution.

9. The process as claimed in claim 1, wherein during the growth phase the evaporation rate by mass is between 0.01 and 0.05 kg of solvent/h/kg of initial stock solution.

* * * * *